(12) United States Patent
Herold et al.

(10) Patent No.: US 8,138,179 B2
(45) Date of Patent: Mar. 20, 2012

(54) SPIRO-IMIDAZO COMPOUNDS

(75) Inventors: Peter Herold, Allschwil (CH); Robert Mah, Allschwil (CH); Vincenzo Tschinke, Allschwil (CH); Aleksandar Stojanovic, Allschwil (CH); Christiane Marti, Allschwil (CH); Stjepan Jelakovic, Allschwil (CH); Bibia Bennacer, Allschwil (CH); Stefan Stutz, Allschwil (CH)

(73) Assignee: Novartis AG, Basel (CH)

( * ) Notice: Subject to any disclaimer, the term of this patent is extended or adjusted under 35 U.S.C. 154(b) by 623 days.

(21) Appl. No.: 12/226,215

(22) PCT Filed: Apr. 12, 2007

(86) PCT No.: PCT/EP2007/053584
§ 371 (c)(1),
(2), (4) Date: Oct. 10, 2008

(87) PCT Pub. No.: WO2007/116098
PCT Pub. Date: Oct. 18, 2007

(65) Prior Publication Data
US 2009/0192145 A1    Jul. 30, 2009

(30) Foreign Application Priority Data
Apr. 12, 2006   (CH) ......................................... 619/06

(51) Int. Cl.
*A61K 31/535*   (2006.01)
*C07D 265/00*   (2006.01)
(52) U.S. Cl. ........................................ 514/229.5; 544/71
(58) Field of Classification Search ........................ None
See application file for complete search history.

(56) References Cited

FOREIGN PATENT DOCUMENTS

| JP | 63-145286 | 6/1988 |
|---|---|---|
| WO | 2004/014914 | 2/2004 |
| WO | 2005/118557 | 12/2005 |
| WO | 2005/118581 | 12/2005 |
| WO | 2006/128851 | 12/2006 |
| WO | 2006/128852 | 12/2006 |
| WO | 2006/128853 | 12/2006 |

OTHER PUBLICATIONS

Nishikaza. Circulation, 2004, 2857-2861.*
"Hyperaldosteronism", http://www.nlm.gov/medlineplus/ency/article/000330.htm, accessed May 21, 2011.*
"Heart failure-Prevention", http://www.mayoclinic.com/health/heart-failure/DS00061/DSECTION=prevention, accessed May 21, 2011.*
International Search Report dated Jul. 2, 2007 in the International (PCT) Application PCT/EP2007/053584 of which the present application is the U.S. National Stage.
PCT Written Opinion dated Jul. 2, 2007 in the International (PCT) Application PCT/EP2007/053584 of which the present application is the U.S. National Stage.

* cited by examiner

*Primary Examiner* — Noble Jarrell
(74) *Attorney, Agent, or Firm* — Wenderoth, Lind & Ponack, L.L.P.

(57) ABSTRACT

Novel heterocyclic compounds of the general formula (I) and salts, preferably pharmaceutically acceptable salts, thereof, in which R, $R^1$, $R^{1'}$, Q, m and n have the meanings explained in detail in the description, a process for their preparation and the use of these compounds as medicaments, in particular as aldosterone synthase inhibitors.

11 Claims, No Drawings

SPIRO-IMIDAZO COMPOUNDS

FIELD OF THE INVENTION

The invention relates to novel heterocyclic compounds, processes for preparing the compounds, pharmaceutical products containing them, and their use as active pharmaceutical ingredients, especially as aldosterone synthase inhibitors.

DETAILED DESCRIPTION OF THE INVENTION

The present invention relates firstly to compounds of the general formula

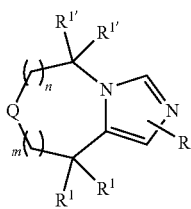

(I)

in which
R is deuterium, halogen or hydrogen;
a) $R^1$ is in each case hydrogen, and $R^{1'}$ and $R^{1'}$ are together a radical of the formula

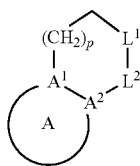

(II)

or
b) $R^1$ and $R^1$ are together a radical of the formula

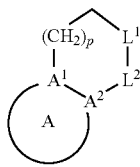

(II)

and $R^{1'}$ is in each case hydrogen,
and for both a) and b):
$A^1$ and $A^2$ are two ortho ring atoms, and A is aryl or heterocyclyl, which radicals may be substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$-alkylsilyl, trifluoro-methoxy or trifluoromethyl;
$L^1$ is —$CH_2$—, —$CH_2$—$CH_2$—, —CH=CH—, —CH=N—, —$CH_2$—CH=N—, —CH=N—O—, —$CH_2$—CH=N—O—, —$CH_2$—O—, —$CH_2$—$CH_2$—O—, —$CH_2$—CH=CH—O—, —$CH_2$—S—, —$CH_2$—$CH_2$—S—, —CH=CH—S—, —$CH_2$—NH—, —$CH_2$—$CH_2$—NH—, —CH=CH—NH—, —$CH_2$—NH—O—, —$CH_2$—$CH_2$—NH—O—, —CH=CH—NH—O—, —$CH_2$—O—NH—, —$CH_2$—$CH_2$—O—NH—, —CH=CH—O—NH—, —$CH_2$—N=N—, —$CH_2$—$CH_2$—N=N—, —CH=CH—N=N—, —$CH_2$—S(O)—, —$CH_2$—$CH_2$—S(O)—, —CH=CH—S(O)—, —$CH_2$—$SO_2$—, —$CH_2$—$CH_2$—$SO_2$, —CH=CH—$SO_2$—, —O—, —S—, —NH—, —NH—O—, —O—NH—, —N=N—, —S(O)— or —$SO_2$—, which radicals may optionally be substituted by 1-3 $R^3$;
$L^2$ is —$CH_2$—, —$CH_2$—$CH_2$—, —CH=CH— or, if $L^1$ is —$CH_2$—, —$CH_2$—$CH_2$— or —CH=CH—, is also —N=CH—, —N=CH—$CH_2$—, —O—N=CH—$CH_2$ or —O—N=CH—, which radicals may optionally be substituted by 1-3 $R^3$ or, if $L^1$ is not —O—, —S—, —NH—, —NH—O—, —O—NH—, —N=N—, —S(O)— or —$SO_2$—, is also a bond;
$R^3$ is $C_1$-$C_8$ alkoxy, $C_1$-$C_8$ alkoxycarbonyl, $C_1$-$C_8$ alkyl, $C_0$-$C_8$ alkylcarbonyl or $C_1$-$C_8$ alkylsulphonyl;
Q is oxygen or sulphur;
m is a number 0, 1 or 2;
n is a number 0, 1 or 2;
p is a number 0, 1, 2, 3 or 4;
where
m and n are not simultaneously 0 and, if $R^1$ is hydrogen, n is 1 or 2;
and their salts, preferably their pharmaceutically acceptable salts.

The linkage of the abovementioned substituents $L^1$ and $L^2$ within the radical of the formula (II) starts from $A^2$ with the substituents $L^2$ and $L^1$ being arranged from left to right when written as indicated above. For example, the fragment "-$A^2$-$L^2$-$L^1$-" of the radical of the formula (II) with $L^1$ meaning "—CH=CH—O—" and with $L^2$ meaning "—$CH_2$—$CH_2$—" is: "-$A^2$-$CH_2$—$CH_2$—CH=CH—O—".

The term aryl stands for a mono-, bi- or tricyclic aromatic hydrocarbon which generally comprises 6-14, preferably 6-10, carbon atoms and is for example phenyl, naphthyl, e.g. 1- or 2-naphthyl or anthracenyl. Aryl having 6-10 carbon atoms, in particular phenyl or 1- or 2-naphthyl, is preferred. The stated radicals may be unsubstituted or substituted one or more times, e.g. once or twice, in which case the substituent may be in any position, e.g. in the o, m or p position of the phenyl radical or in the 3 or 4 position of the 1- or 2-naphthyl radical, and there may also be a plurality of identical or different substituents present. Examples of substituents on aryl radicals or the preferred phenyl or naphthyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, tri-$C_1$-$C_4$ alkylsilyl, trifluoromethoxy or trifluoromethyl.

Aryl-$C_0$-$C_4$ alkyl is for example phenyl, naphthyl or benzyl.

The term heterocyclyl stands for a saturated, partially saturated or unsaturated, 4-8-membered, particularly preferably 5-membered, monocyclic ring system, for a saturated, partially saturated or unsaturated, 7-12-membered, particularly preferably 9-10-membered, bicyclic ring system and also for a partially saturated or unsaturated, 9-14-membered tricyclic ring system which comprises an N, O or S atom in at least one of the rings, it being possible for an additional N, O or S atom to be present in one ring. Said radicals may be unsubstituted or substituted one or more times, e.g. once or twice, and there may also be a plurality of identical or different substituents present. Examples of substituents on heterocyclyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl.

Saturated heterocyclyl-$C_0$-$C_4$ alkyl is for example azepanyl, azetidinyl, aziridinyl, 3,4-dihydroxypyrrolidinyl, 2,6-dimethylmorpholinyl, 3,5-dimethylmorpholinyl, dioxanyl, [1,4]dioxepanyl, dioxolanyl, 4,4-dioxothiomorpholinyl, dithianyl, dithiolanyl, 2-hydroxymethylpyrrolidinyl, 4-hydroxypiperidinyl, 3-hydroxypyrrolidinyl, 4-methylpiperazinyl, 1-methylpiperidinyl, 1-methylpyrrolidinyl, morpholinyl, oxathianyl, oxepanyl, 2-oxo-azepanyl, 2-oxo-imidazolidinyl, 2-oxo-oxazolidinyl, 2-oxo-piperidinyl, 4-oxopiperidinyl, 2-oxo-pyrrolidinyl, 2-oxo-tetrahydropyrimidinyl, 4-oxo-thiomorpholinyl, piperazinyl, piperidinyl, pyrrolidinyl, tetrahydrofuranyl, tetrahydropyranyl, tetrahydrothiophenyl, tetrahydrothiopyranyl, thiepanyl or thiomorpholinyl.

Partially saturated bicyclic heterocyclyl-$C_0$-$C_4$ alkyl is for example 3,4-dihydro-2H-benzo[1,4]oxazinyl, 4,5,6,7-tetrahydrobenzofuranyl or 4,5,6,7-tetrahydrobenzothiazolyl.

Unsaturated bicyclic heterocyclyl-$C_0$-$C_4$ alkyl is for example benzofuranyl, benzoimidazolyl, benzo[d]isothiazolyl, benzo[d]isoxazolyl, benzo[b]thiophen-yl, quinolinyl, imidazo[1,5-a]pyridinyl, indazolyl, indolyl or isoquinolinyl.

Unsaturated monocyclic heterocyclyl-$C_0$-$C_4$ alkyl is for example imidazolyl, oxazolyl, pyridyl, pyrrolyl, tetrazolyl, thiazolyl or thiophenyl.

$C_1$-$C_8$-alkoxy is for example $C_1$-$C_5$-alkoxy such as methoxy, ethoxy, propoxy, isopropoxy, butoxy, isobutoxy, secondary butoxy, tertiary butoxy or pentoxy, but may also be a hexoxy or heptoxy group.

$C_1$-$C_8$ alkoxycarbonyl is preferably $C_1$-$C_4$ alkoxycarbonyl such as methoxycarbonyl, ethoxycarbonyl, propoxycarbonyl, isopropoxycarbonyl, butoxycarbonyl, isobutoxycarbonyl, secondary butoxycarbonyl or tertiary butoxycarbonyl.

$C_1$-$C_8$-alkyl may be straight-chain or branched and/or bridged and is for example methyl, ethyl, propyl, isopropyl, butyl, isobutyl, secondary butyl, tertiary butyl, or a pentyl, hexyl or heptyl group.

$C_0$-$C_8$ alkylcarbonyl is for example formyl, acetyl, propionyl, propylcarbonyl, isopropylcarbonyl, butylcarbonyl, isobutylcarbonyl, secondary butylcarbonyl or tertiary butylcarbonyl.

Halogen is for example fluorine, chlorine, bromine or iodine.

The compound groups mentioned below are not to be regarded as closed; on the contrary, parts of these compound groups may be replaced by one another or by the definitions given above, or be omitted, in a meaningful way, e.g. to replace general by more specific definitions. The definitions mentioned apply within the scope of general chemical principles such as, for example, the usual valencies of atoms.

R is preferably deuterium or hydrogen.

A is preferably optionally substituted 4-acetylphenyl, 4-cyanophenyl, 4-methanesulphonylphenyl, 4-methoxyphenyl, 4-nitrophenyl, 4-heterocyclylphenyl, where the heterocycle preferably comprises at least one nitrogen atom, or pyridyl.

The group -$L^1$-$L^2$- is preferably $C_1$-$C_4$-alkylene which is optionally substituted by 1-3 $C_1$-$C_8$ alkoxy, $C_1$-$C_8$ alkoxycarbonyl, $C_1$-$C_8$ alkyl, $C_0$-$C_8$ alkylcarbonyl or $C_1$-$C_8$ alkylsulphonyl.

p is preferably a number 0 or 1. p is particularly preferably the number 0.

n is preferably a number 0 or 1. n is particularly preferably the number 1.

Preferred substituents for aryl or heterocyclyl are $C_1$-$C_8$ alkoxy, $C_1$-$C_8$ alkyl, $C_1$-$C_8$ alkylcarbonyl, $C_1$-$C_8$ alkylsulphonyl, optionally substituted aryl, cyano, halogen, optionally substituted heterocyclyl, nitro, oxide, trifluoromethyl, trifluoromethoxy or trimethylsilanyl. Very particularly preferred substituents for aryl or heterocyclyl are acetyl, bromine, chlorine, cyano, fluorine, methanesulphonyl, methoxy, nitro, oxazolyl, oxide, optionally substituted phenyl, optionally substituted tetrazolyl, optionally substituted thiazolyl or optionally substituted thiophenyl.

It is likewise preferred for A to be a mono-, di- or tri-substituted unsaturated heterocyclyl substituent, where the substituents are preferably selected from the group consisting of $C_1$-$C_8$ alkyl, $C_1$-$C_8$ alkoxy, $C_1$-$C_8$ alkoxycarbonyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy and trifluoromethyl.

Particularly preferred compounds of the formula (I) are those of the general formula (Ia)

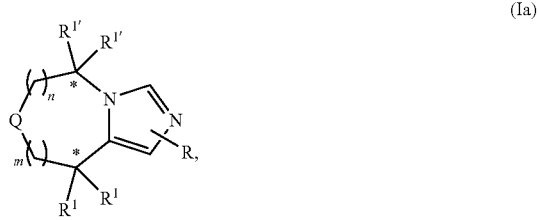

(Ia)

and salts, preferably pharmaceutically acceptable salts, thereof, in which R, $R^1$, $R^{1'}$, Q, m and n have the meanings indicated above for compounds of the formula (I), and where the above preferences apply analogously.

* designates an asymmetric carbon atom at the C atom for which the respective pairs of $R^1$ and $R^{1'}$ substituents are not both hydrogen.

The compounds of the formula (I) or (Ia) which possess at least one asymmetric carbon atom can exist in the form of optically pure enantiomers, mixtures of enantiomers, or racemates. Compounds having a second asymmetric carbon atom can exist in the form of optically pure diastereomers, mixtures of diastereomers, diastereomeric racemates, mixtures of diastereomeric racemates, or meso compounds. The invention embraces all of these forms. Mixtures of enantiomers, racemates, mixtures of diastereomers, diastereomeric racemates, or mixtures of diastereomeric racemates can be fractionated by conventional methods, such as by racemate resolution, column chromatography, thin-layer chromatography, HPLC and the like.

The compounds of the formula (Ia) have at least one asymmetric carbon atom, which is labelled "*". A compound of the formula (Ia) is to be understood as a compound having a specific configuration around the designated asymmetric carbon atom. If a synthesis method is used which leads to racemic compounds, the racemate resolution is carried out in accordance with conventional methods, such as via a chiral HPLC column. Compounds of the formula (Ia) as described in the present invention exhibit a pronounced aldosterone synthase and/or 11-β-hydroxylase inhibitory activity and a low aromatase inhibitory activity. The aforementioned aldosterone synthase activity can, readily and as described below, be determined via cellular assays based on the NCI-H295R human adrenocortical carcinoma cell line. The aforementioned aromatase inhibitory activity can, as the skilled worker is well aware and as described below, be determined using the commercial Cyp19 enzyme inhibition kit, preferably the Cyp19/methoxy-4-trifluoromethyl-coumarin (MFC) high throughput inhibition kit (Becton Dickinson Biosciences, San Jose, Calif., USA) as described hereafter. In the above-mentioned assay systems, preferred compounds of the formula (Ia) show an aldosterone synthase activity which is at least 5 times higher, but preferably 10 times higher, or more preferably 20 times higher than the substances of the formula (Ia) with the opposite configuration around the asymmetric carbon atom labelled "*". A higher inhibiting activity corresponds to a lower $IC_{50}$ value.

The expression "pharmaceutically acceptable salts" embraces salts with organic or inorganic acids, such as hydrochloric acid, hydrobromic acid, nitric acid, sulphuric acid, phosphoric acid, citric acid, formic acid, maleic acid, acetic acid, succinic acid, tartaric acid, methanesulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) or (Ia) can be prepared in an analogous manner to the preparation processes disclosed per se in the literature, J. Med. Chem. 43 (25), (2003), pp. 5445-5457 (Scheme I).

Scheme I:

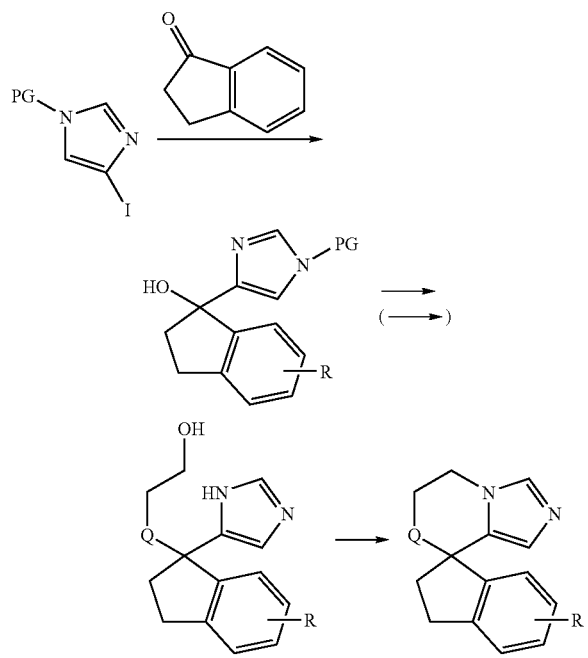

The compounds of the formula (I) or (Ia) can likewise be obtained in an analogous manner to the preparation processes disclosed per se in the literature starting from suitably substituted 2-aminoethanols, which can be converted for example in analogy to Org. Lett. 7 (5), (2005), pp. 937-939, into 5-spiro-morpholin-3-ones which are then converted in analogy to the process disclosed in U.S. Pat. No. 4,401,597 into compounds of the formula (I) or (Ia) (Scheme II).

Scheme II:

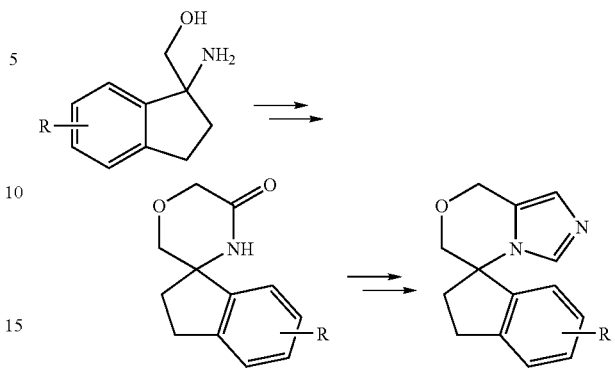

Details of the specific preparation variants can be found in the examples.

The compounds of the formula (I) or (Ia) can also be prepared in optically pure form. Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+) or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically useful or non-toxic salts of compounds of the formula (I) or (Ia). Such salts are formed for example by compounds of the formula (I) or (Ia) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxyl-lower alkyl)amines, such as ethanolamine, diethanolamine or triethanolamine, tris(hydroxylmethyl)methylamine or 2-hydroxyl-tertiary-butylamine, N,N-di-lower alkyl-N-(hydroxy-lower alkyl)amine, such as N,N-di-N-dimethyl-N-(2-hydroxyl-ethyl)amine, or N-methyl-D-glucamine, or quaternary ammonium hydroxides, such as tetrabutylammonium hydroxide. The compounds of the formula (I) or (Ia) containing a basic group, such as an amino group, can form acid addition salts, with suitable inorganic acids for example, such as hydrohalic acid, such as hydrochloric acid, hydrobromic acid, or sulphuric acid with replacement of one or both protons, phosphoric acid with replacement of one or more protons, orthophosphoric acid or metaphosphoric acid for example, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxylmaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as the α-amino acids specified earlier on, and also methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) or (Ia) containing acidic and basic groups can also form inner salts.

Isolation and purification can also be carried out using pharmaceutically unsuitable salts.

The compounds of the formula (I) or (Ia) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)-alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the close relationship between a free compound, a prodrug derivative and a salt compound, a defined compound in this invention also includes its prodrug derivative and salt form, insofar as this is possible and appropriate.

Aldosterone is a steroidal hormone which is synthesized in the zona glomerulosa cells of the adrenal cortex by the enzyme aldosterone synthase (CYP11B2). Aldosterone production and secretion is regulated by the adrenocorticotropic hormone (ACTH), angiotensin II, potassium and sodium ions. The primary biological function of aldosterone is the regulation of the salt balance, with aldosterone controlling the reabsorption of sodium ions from the renal filtrate and the secretion of potassium ions into the renal filtrate. The state of excessive aldosterone secretion, also called hyperaldosteronism, can lead to high blood pressure, hypokalaemia, alkalosis, muscle weakness, polyuria, polydipsia, oedemas, vasculitis, increased collagen formation, fibrosis and endothelial dysfunction.

The chemical compounds described in this invention inhibit the cytochrome P450 enzyme aldosterone synthase (CYP11B2) and can therefore be used to treat states induced by aldosterone. The compounds described can be employed for preventing, for delaying the progression of or treating states such as hypokalaemia, hypertension, congestive heart failure, acute and—in particular—chronic renal failure, cardiovascular restenosis, atherosclerosis, metabolic syndrome (syndrome X), adiposity (obesity), vasculitis, primary and secondary hyperaldosteronism, nephropathy, myocardial infarction, coronary heart disease, increased collagen formation, fibrosis, vascular and coronary tissue changes (remodelling) secondary to high blood pressure, endothelial dysfunction, and oedemas secondary to cirrhosis, nephrosis and congestive heart failure.

Cortisol is a steroidal hormone which is synthesized almost exclusively in the zona fasciculata cells of the adrenal cortex by the cytochrome P450 enzyme 11-β-hydroxylase (CYP11B1). Cortisol production is regulated by ACTH. The primary biological function of cortisol is to regulate the production and the provision of carbohydrates for the brain and other metabolically active tissues. Increased cortisol production and secretion is a normal physiological response to stress and leads to the essential mobilization of fats, proteins and carbohydrates to cover increased physical energy demand. Chronically excessive cortisol release describes the condition of Cushing's syndrome. Cushing's syndrome may come about on the one hand as a result of cortisol hypersynthesis, which may be generated by an adrenocortical tumour, or on the other hand as the consequence of excessive stimulation of the adrenal cortex by ACTH. The first form is referred to as primary hypercortisolism, the second form as secondary hypercortisolism. An excessive and persistent cortisol secretion may also accompany a stress response, which can lead to depression and the suppression of the immune system.

The chemical compounds described in this invention inhibit the enzyme 11-β-hydroxylase (CYP11B1) and may therefore, owing to the inhibition of cortisol synthesis, be employed for preventing, for delaying the progression of or treating Cushing's syndrome and also the physical and mental consequences of excessive and persistent cortisol secretion in states of stress.

The inhibition of aldosterone synthase (CYP11B2), as well as 11-β-hydroxylase (Cyp11B1) and aromatase (Cyp19) by herein described compounds may be measured by the following in vitro assay.

The cell line NCI-H295R was originally derived from an adrenal carcinoma and was subsequently characterized in the literature for the inducible secretion of steroidal hormones and the presence of the key enzymes necessary for steroidogenesis. These include Cyp11A (cholesterol side-chain cleavage), Cyp11B1 (steroid 11β-hydroxylase), Cyp11B2 (aldosterone synthase), Cyp17 (steroid 17α-hydroxylase and 17,20 lyase), Cyp19 (aromatase), Cyp21B2 (steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-H295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferrin, selenit (I-T-S, Becton Dickinson Biosciences, Franklin Lakes, N.J., USA) and antibiotics in 75 cm$^2$ cell culture flasks at a temperature of 37° C. and a 95% air/5% $CO_2$ humidified atmosphere. The cells are subsequently transferred to a 24-well plate and seeded in the presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence of cell stimulatory agents. The test compound is added in a concentration range of 0.2 nanomolar to 20 micromolar. Angiotensin-II (e.g. at 10 or 100 nanomolar concentration), potassium ions (e.g. at 16 millimolar), forskolin (e.g. at 10 micromolar) or a combination of two agents may serve as cell-stimulatory agents. The cellular secretion of aldosterone, cortisol, corticosterone and estradiol/estrone into the cell culture medium can be quantitatively assessed with commercially available radioimmunoassays and specific anti-bodies (e.g. Diagnostics Products Corporation, Los Angeles, Calif., USA) according to the manufacturer's instructions.

The degree of secretion of a selective steroid is used as a measure of enzyme activity, respectively enzyme inhibition, in the presence or absence of a test compound. The dose-dependent enzyme inhibitory activity of a compound is reflected in an inhibition curve that is characterized by an $IC_{50}$ value. The $IC_{50}$ values for active test compounds are generated by simple linear regression analysis to establish inhibition curves without data weighting. The inhibition curve is generated by fitting a 4-parameter logistic function to the raw data of the samples using the least squares approach. The function is described as follows:

$$Y=(d-a)/((1+(x/c)^{-b})+a)$$

with:
a=minimum
b=slope
c=$IC_{50}$
d=maximum
x=inhibitor concentrations

The compounds of the present invention show in the herein described in vitro test systems inhibitory activities with $IC_{50}$ values for aldosterone synthesis inhibition ranging from $10^{-4}$ to $10^{-10}$ mol/l, and $IC_{50}$ values for cortisol synthesis inhibition ranging from $10^{-4}$ to $10^{-10}$ mol/l.

Additionally, the in vitro inhibition of aromatase activity of the compounds of the present invention can be demonstrated by using a commercial Cyp19 enzyme inhibition kit. The Cyp19/methoxy-4-trifluoromethyl-coumarin (MFC) high throughput inhibition kit (Becton Dickinson Biosciences, San Jose, Calif., USA), for example, is designed to screen for potential inhibitors of Cyp19 catalytic activity in a 96-well format. The kit includes recombinant human Cyp19 enzyme in the form of supersomes, a fluorescent P450 substrate, an NADPH regenerating system, a reaction buffer and a stop reagent. MFC, the fluorogenic substrate is rapidly converted by Cyp19 supersomes to the highly fluorescent product 7-hydroxy-4-trifluoromethyl coumarin (7-HFC). The execution of the assay in the presence of various concentrations of inhibitor compounds ranging from 0.2 nanomolar to 20 millimolar occurs according to the manufacturer's instructions.

The inhibition curve is generated by fitting a 4-parameter logistic function to the raw data of the samples using the least squares approach. The function is described as follows:

$$Y=(d-a)/((1+(x/c)^{-b})+a)$$

with:
a=minimal data values
b=slope
c=$IC_{50}$
d=maximal data values
x=inhibitor concentrations The aldosterone- and corticosterone-suppressing activity of herein described compounds may be assessed with the following in vivo protocol.

Adult male Wistar rats weighing between 250 and 350 grams are kept under the usual 12 hour light and 12 hour dark conditions at a temperature of 23° C.±2° C. On the first day of the experiment, the animals receive a subcutaneous injection of a depot ACTH product in a dose of 1.0 mg/kg weight (SYNACTHEN-Depot, Novartis, Basel, CH) 16 hours prior to the administration of a test compound. Pilot studies showed that this ACTH dose significantly increased plasma aldosterone and corticosterone levels by 5- to 20-fold over a period of at least 18 hours. An alternative method to stimulate aldosterone secretion consists in subjecting rats to a low salt diet for 48 hours and applying the diuretic furosemide at 10 mg/kg by subcutaneous or intraperitoneal administration 16 hours, respectively 2 hours prior to the start of the experiment. On the second day of the experiment, the animals are divided into test groups of 5 animals and subjected to a first bleed 1 hour prior to the administration of test compound. Subsequently, and 16 hours after the injection of the ACTH product, the animals receive either vehicle or test compound dissolved in vehide in a variable dose range from 0.02 to 20 mg/kg by oral gavage. The animals are bled two more times from the vena subclavia under isoflurane anaesthesia 2 and 6 hours after dosing. The blood is collected in heparin-treated tubes. The plasma samples are obtained by centrifugation and stored at −20° C. An alternative method to bleed animals time-dependently consists in using animals that are chronically carotid catheterized which allows the periodical sampling of up to 0.2 ml of blood using an AccuSampler (DiLab Europe, Lund, Sweden). The blood sampling with the AccuSampler may occur 1 hour prior to the administration of a test compound and 2, 4, 6, 8, 12, 16 and 24 hours thereafter. The blood samples are anticoagulated with heparin and centrifuged. The aldosterone and corticosterone concentrations of the plasma samples can be determined with a radioimmunoassay as described above for the in vitro test systems.

The selective suppression of plasma steroid levels as for instance aldosterone in comparison to corticosterone may serve as a measure for in vivo bioavailability and pharmacodynamic enzyme inhibitory activity of the herein described compounds. The evaluation of the data may occur relative to the application of vehicle or quantitatively by determination of the area under the curve (AUC).

Examples of suppression of aldosterone and corticosterone levels:

| Compound of Example | Dose (mg/kg p.o.) | Aldosterone levels (% change[+] at 2 h) | Corticosterone levels (% change[+] at 2 h) |
|---|---|---|---|
| 10 | 4 | −81.7 | −14.5 |

[+]The resulting changes in plasma aldosterone, respectively corticosterone, levels upon oral administration of a test compound are expressed as percent (%) change that is defined by the ratio of the [(plasma steroid level 2 hours after compound administration) − (plasma steroid level 1 hour prior to compound administration)] divided by (plasma steroid level 1 hour prior to compound administration).

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatine capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatine, disintegrants such as potato starch or crosslinked polyvinylpyrrolidone (PVPP) and lubricants such as stearic acid or magnesium stearate.

Examples of excipients suitable for soft gelatine capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The compounds of the invention described herein permit the following methods of use:

- as therapeutic combination in the form of a product or of a kit which is composed of individual components consisting of a compound described herein, in free form or as pharmaceutically acceptable salt, and at least one pharmaceutical form whose active ingredient has a blood pressure-lowering, an inotropic, an antidiabetic, an obesity-reducing or a lipid-lowering effect, which can be used either simultaneously or sequentially. The product and the kit may comprise instructions for use.
- as method for combined use, such as, for example, in simultaneous or sequential succession, of a therapeutically effective amount of a compound described herein, in free or in pharmaceutically acceptable salt form, and of a second active ingredient with blood pressure-lowering, inotropic, antidiabetic, obesity-reducing or lipid-lowering effect.

The compounds described herein and their pharmaceutically acceptable salts can be used in combination with (i) one or more blood pressure-lowering active ingredients, as such for example:
  renin inhibitors such as aliskiren;
  angiotensin II receptor blockers such as candesartan, irbesartan, olmesartan, losartan, valsartan, telmisartan etc.;
  ACE inhibitors such as quinapril, ramipril, trandolapril, lisinopril, captopril, enalapril etc.;
  calcium antagonists such as nifedipine, nicardipine, verapamil, isradipine, nimodipine, amlodipine, felodipine, nisoldipine, diltiazem, fendiline, flunarizine, perhexyline, gallopamil etc.;
  diuretics such as hydrochlorothiazide, chlorothiazide, acetazolamide, amiloride, bumetanide, benzthiazide, etacrynic acid, furosemide, indacrinone, metolazone, triamterene, chlorthalidone, etc.;
  aldosterone receptor blockers such as spironolactone, eplerenone;
  endothelin receptor blockers such as bosentan;
  phosphodiesterase inhibitors such as aminone, sildenafil;
  direct vasodilators such as dihydralazine, minoxidil, pinacidil, diazoxide, nitroprusside, flosequinan etc.;
  α- and β-receptor blockers such as phentolamine, phenoxybenzamine, prazosin, doxazosin, terazosin, carvedilol, atenolol, metoprolol, nadolol, propranolol, timolol, carteolol etc.;
  neutral endopeptidase (NEP) inhibitors;
  sympatholytics such as methyldopa, clonidine, guanabenz, reserpine;

(ii) one or more agents having inotropic activity, as such for example:
  cardiac glycosides such as digoxin;
  β-receptor stimulators such as dobutamine;
  thyroid hormone such as thyroxine;

(iii) one or more agents having antidiabetic activity, as such for example:
  insulins such as insulin aspart, insulin human, insulin lispro, insulin glargine and further fast-, medium- and long-acting insulin derivatives and combinations;
  insulin sensitizers such as rosiglitazone, pioglitazone;
  sulphonylureas such as glimepiride, chlorpropamide, glipizide, glyburide etc.;
  biguanides such as metformin;
  glucosidase inhibitors such as acarbose, miglitol;
  meglitinides such as repaglinide, nateglinide;

(iv) one or more obesity-reducing ingredients, as such for example:
  lipase inhibitors such as orlistat;
  appetite suppressants such as sibutramine, phentermine;

(v) one or more lipid-lowering ingredients, such as, for example,
  HMG-CoA reductase inhibitors such as lovastatin, fluvastatin, pravastatin, atorvastatin, simvastatin, rosuvastatin etc.;
  fibrate derivatives such as fenofibrate, gemfibrozil etc.;
  bile acid-binding active ingredients such as colestipol, colestyramine, colesevelam;
  cholesterol absorption inhibitors such as ezetimibe;
  nicotinic acid such as niacin and other agents which are suitable for the treatment of high blood pressure, heart failure or vascular disorders associated with diabetes and renal disorders, such as acute or chronic renal failure, in humans and animals. Such combinations can be used separately or in products which comprise a plurality of components.

The compounds described herein and their pharmaceutically acceptable salts can additionally be used in combination with (i) a diagnostic test system which permits quantitative determination of the plasma aldosterone level (PAC, plasma aldosterone concentration)

(ii) a diagnostic test system which permits quantitative determination of the plasma renin level (PRC, plasma renin concentration)

(iii) a diagnostic test system which permits quantitative determination of the plasma renin activity (PRA, plasma renin activity)

(iv) a diagnostic test system which permits quantitative determination of the plasma aldosterone/renin level (ARC, aldosterone renin concentration)

(v) a diagnostic test system which permits quantitative determination of the plasma aldosterone/renin activity (ARR, aldosterone to renin activity ratio)

(vi) a diagnostic test system which permits quantitative determination of the plasma cortisol level (PCC, plasma cortisol concentration)

Such diagnosis-therapy combinations can be used separately or in products which comprise a plurality of components.

EXAMPLES

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program.

HPLC gradients on Hypersil BDS C-18 (5 μm); column: 4×125 mm:

(I) 90% water*/10% acetonitrile* to 0% water*/100% acetonitrile* in 5 minutes+2.5 minutes (1.5 ml/min)

(II) 99% water*/1% acetonitrile* to 0% water*/100% acetonitrile* in 10 minutes+2 minutes (1.5 ml/min)

HPLC gradients on Synergi 4 μm POLAR-RP 80A; column 4.60×100 mm:

(III) 90% water*/10% acetonitrile* to 0% water*/100% acetonitrile* in 5 minutes+2.5 minutes (1.5 ml/min)

* contains 0.1% trifluoroacetic acid

The abbreviations used are as follows:

Rf ratio of distance traveled by a substance to distance of the eluent from the starting point in thin-layer chromatography Rt retention time of a substance in HPLC (in minutes)

m.p. melting point (temperature)

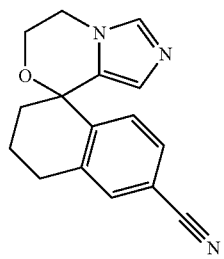

1

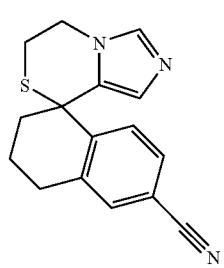

2

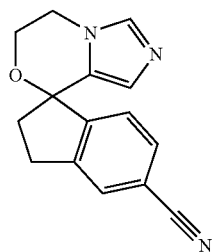

3

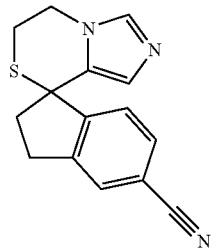

4

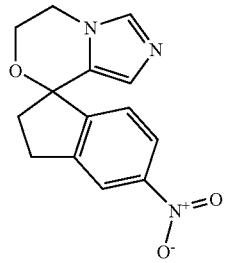

5

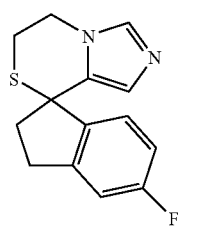

6

-continued

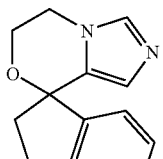

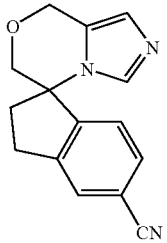

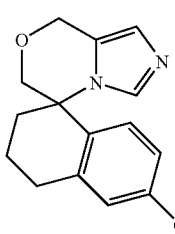

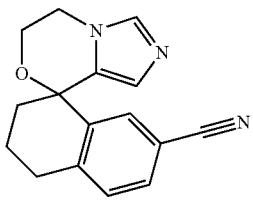

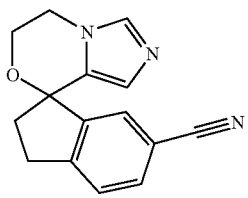

Example 1

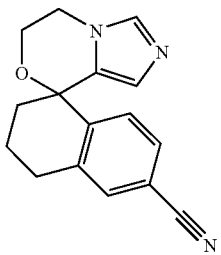

spiro-[(5,6-Dihydro-8H-imidazo[5,1-c][1,4]ox-azine)-8,5'-(5',6',7',8'-tetrahydronaphthalene-2'-carbonitrile)]

A solution of 0.2 mmol of 2-[6-cyano-1-(1-trityl-1H-imidazol-4-yl)-1,2,3,4-tetrahydronaphthalen-1-yloxy]ethyl methanesulphonate in 5 ml of N,N-dimethylformamide is mixed with 1 mmol of caesium carbonate and heated at 80° C. for 3 hours. The reaction mixture is cooled to room temperature, diluted with water and extracted with ethyl acetate (2×). The combined organic phases are dried with sodium sulphate and evaporated. The title compound is identified from the residue on the basis of the Rf by flash chromatography (SiO₂ 60F).

The starting material is prepared as follows:

a1) 2-[6-Cyano-1-(1-trityl-1H-imidazol-4-yl)-1,2,3,4-tetrahydronaphthalen-1-yloxy]ethyl methanesulphonate 5 mmol of triethylamine and 2.0 mmol of methanesulphonyl chloride are added to a solution of 1.0 mmol of 5-(2-hydroxyethoxy)-5-(1-trityl-1H-imidazol-4-yl)-5,6,7,8-tetrahydronaphthalene-2-carbonitrile in 10 ml of dichloromethane at 0° C. The reaction mixture is stirred at 0° C. for 1 hour, diluted with dichloromethane, washed with 1N HCl, dried with sodium sulphate and evaporated. The crude title compound is identified on the basis of the Rf and used without further purification in the next stage.

b1) 5-(2-Hydroxyethoxy)-5-(1-trityl-1H-imidazol-4-yl)-5,6,7,8-tetrahydronaphthalene-2-carbonitrile 3.0 mmol of sodium borohydride are added in portions to a solution of 1.0 mmol of ethyl [6-cyano-1-(1-trityl-1H-imidazol-4-yl)-1,2,3,4-tetrahydronaphthalen-1-yloxy]acetate in 5 ml of ethanol at 20° C. The reaction mixture is stirred at 20° C. for 2-6 hours and then evaporated. The residue is taken up in saturated aqueous sodium bicarbonate solution and dichloromethane, and the mixture is vigorously stirred for 10 minutes. The phases are separated and the aqueous phase is back-extracted with dichloromethane. The combined organic phases are dried with sodium sulphate and evaporated. The title compound is identified from the residue on the basis of its Rf by flash chromatography (SiO₂ 60F).

c1) Ethyl [6-cyano-1-(1-trityl-1H-imidazol-4-yl)-1,2,3,4-tetrahydronaphthalen-1-yloxy]acetate 1.9 mmol of sodium hydride (60% dispersion in oil) are added in portions to a solution of 1.3 mmol of 5-hydroxy-5-(1-trityl-1H-imidazol-4-yl)-5,6,7,8-tetrahydronaphthalene-2-carbonitrile in 10 ml of tetrahydrofuran, and the mixture is stirred under reflux for 1 hour. 3.0 mmol of ethyl bromoacetate [105-36-2] are added and the reaction mixture is stirred under reflux for 8-16 hours. The reaction mixture is cooled and poured into saturated sodium bicarbonate solution and extracted with tert-butyl methyl ether (2×). The combined organic phases are washed with water and brine, dried with sodium sulphate and evaporated. The title compound is identified from the residue on the basis of its Rf by flash chromatography (SiO₂ 60F).

d1) 5-Hydroxy-5-(1-trityl-1H-imidazol-4-yl)-5,6,7,8-tetrahydronaphthalene-2-carbonitrile 12 mmol of ethylmagnesium chloride (3M in diethyl ether) are added to a solution of 10 mmol of 4-iodo-1-trityl-1H-imidazole [96797-15-8] in 40 ml of dichloromethane. The mixture is stirred for 45 minutes, and a solution of 10 mmol of 5-oxo-5,6,7,8-tetrahydronaphthalene-2-carbonitrile [90401-84-6] in 15 ml of dichloromethane is added. The reaction mixture is stirred at room temperature overnight and quenched with saturated ammonium chloride solution. The phases are separated, and the aqueous phase is extracted with dichloromethane (3×). The combined organic phases are washed with brine, dried with sodium sulphate and evaporated. The title compound is identified from the residue on the basis of the Rf by flash chromatography (SiO$_2$ 60F).

Alternative Synthesis for Example 1:

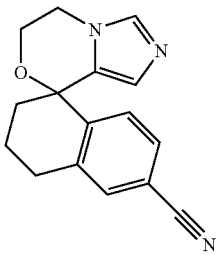

spiro-[(5,6-Dihydro-8H-imidazo[5,1-c][1,4]oxazine)-8,5'-(5',6',7',8'-tetrahydronaphthalene-2'-carbonitrile)]

1.00 mmol of spiro-[(5,6-dihydro-8H-imidazo[5,1-c][1,4]oxazine)-8,5'-(6'-iodo-5',6',7',8'-tetrahydronaphthalene-2'-carbonitrile)] is added to a suspension of a spatula tip of Raney nickel in 5 ml of methanol. The reaction mixture is then hydrogenated under atmospheric pressure at room temperature for 2-6 hours. The catalyst is filtered off through Hyflo, the filter cake is washed with methanol, and the filtrate is evaporated. The title compound is obtained from the residue by flash chromatography (SiO$_2$ 60F). Rf=0.19 (dichloromethane-ammonia 2M in ethanol 95:5); Rt=5.40 (gradient II).

The starting materials are prepared as follows:

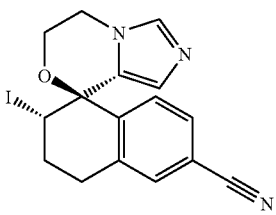

a2) spiro-[(5,6-Dihydro-8H-imidazo[5,1-c][1,4]oxazine-8,5'-(6'-iodo-5',6',7',8'-tetrahydronaphthalene-2'-carbonitrile)]

A solution of 4.00 mmol of 5-[3-(2-hydroxyethyl)-3H-imidazol-4-yl]-7,8-dihydronaphthalene-2-carbonitrile in 30 ml of dioxane is mixed with 6 ml of water and 20.0 mmol of silver trifluoroacetate. A solution of 20.0 mmol of iodine in 50 ml of dioxane is added dropwise over the course of 1 hour at room temperature, and the resulting suspension is then stirred at room temperature for 16 hours. The solid is filtered off through Hyflo, the filter cake is washed with ethyl acetate, and the filtrate is washed with saturated aqueous sodium thiosulphate solution and brine, dried with sodium sulphate and evaporated. The title compound is obtained as a yellowish solid from the residue by flash chromatography (SiO$_2$ 60F). Rf=0.25 (dichloromethane-ammonia 2M in ethanol 95:5); Rt=5.90 (gradient II).

b2) 5-[3-(2-Hydroxyethyl)-3H-imidazol-4-yl]-7,8-dihydronaphthalene-2-carbonitrile 43.0 mmol of sodium borohydride are added in portions to a solution of 19.5 mmol of ethyl [5-(6-cyano-3,4-dihydronaphthalen-1-yl)imidazol-1-yl]acetate in 150 ml of ethanol at 0° C. The reaction mixture is stirred at room temperature for 2 hours and then evaporated. The residue is taken up in saturated aqueous sodium bicarbonate solution, and dichloromethane is added to the mixture. The reaction mixture is stirred at room temperature for 10 minutes and the phases are separated. The aqueous phase is back-extracted with dichloromethane, and the combined organic phases are washed with brine, dried with sodium sulphate and evaporated. The title compound is obtained as a white solid from the residue by flash chromatography (SiO$_2$ 60F). Rf=0.16 (dichloromethane-methanol-25% aqueous ammonia solution 200:20:1); Rt=5.04 (gradient II).

c2) Ethyl [5-(6-cyano-3,4-dihydronaphthalen-1-yl)imidazol-1-yl]acetate

A mixture of 16.0 mmol of 5-(4,4,5,5-tetramethyl-[1,3,2]dioxaborolan-2-yl)-7,8-dihydronaphthalene-2-carbonitrile, 18.0 mmol of (5-iodoimidazol-1-yl)acetate (Example 1f2), 0.74 mmol of tetrakis(triphenylphosphine)palladium(0) and 16 ml of 2M aqueous sodium carbonate solution in 100 ml of dioxane is heated at 80° C. for 5 hours. The reaction mixture is cooled, poured into water and extracted with tert-butyl methyl ether. The combined organic phases are washed with brine, dried with sodium sulphate and evaporated. The title compound is obtained as a colourless oil from the residue by flash chromatography (SiO$_2$ 60F). Rf=0.11 (dichloromethane-methanol 97:3); Rt=5.90 (gradient II).

d2) 5-(4,4,5,5-Tetramethyl-[1,3,2]dioxaborolan-2-yl)-7,8-dihydronaphthalene-2-carbonitrile 50.0 mmol of 6-cyano-3,4-dihydronaphthalen-1-yl trifluoromethanesulphonate are added to a mixture of 1.50 mmol of bis(triphenylphosphine)palladium(II) chloride, 3.00 mmol of triphenylphosphine, 75.0 mmol of potassium phenolate [100-67-4] and 89.8 mmol of bis(pinacolato)diboron [73183-34-3] in 210 ml of toluene under argon. The reaction mixture is stirred at 50° C. for 4 hours and then cooled to room temperature and poured into ice-cold 1M sodium hydroxide solution. The mixture is extracted with tert-butyl methyl ether, and the combined organic phases are washed with brine, dried with sodium sulphate and evaporated. The title compound is obtained as a white solid from the residue by flash chromatography (SiO$_2$ 60F). Rf=0.19 (ethyl acetate-heptane 1:10); Rt=10.17 (gradient II).

e2) 6-Cyano-3,4-dihydronaphthalen-1-yl Trifluoromethanesulphonate

A solution of 107 mmol of 5-oxo-5,6,7,8-tetrahydronaphthalene-2-carbonitrile [90401-84-6] and 150 mmol of 2,6-di-tert-butyl-4-methylpyridine [38222-83-2] in 380 ml of 1,2-dichloroethane is cooled to 0-5° C. in an ice bath. 123 mmol of trifluoromethanesulphonic anhydride are added dropwise at 0-5° C., and the reaction mixture is then stirred at 0-23° C. for 16 hours. 400 ml of heptane are added to the reaction mixture, and the precipitated solid is filtered off through Hyflo. The filter cake is washed with heptane, and the filtrate is evaporated. The title compound is obtained as a beige solid from the residue by flash chromatography (SiO$_2$ 60F). Rf=0.24 (dichloromethane-heptane 1:1); Rt=7.89 (gradient II).

f2) Ethyl 5-iodoimidazol-1-yl)acetate 170 mmol of ethyl bromoacetate are added to a suspension of 113 mmol of 4-iodo-1-tritylimidazole [96797-15-8] in 450 ml acetonitrile and 90 ml of ethyl acetate. The suspension is then stirred at 80° C. for 7 days. The reaction mixture is evaporated and the residue is taken up in 300 ml of acetic acid-water 2:1 and heated at 50° C. for 1 hour. The reaction mixture is cooled to room temperature, the precipitated solid is filtered off through Hyflo, and the filter cake is washed with acetic acid-water 1:1. The filtrate is concentrated. The residue is taken up in a 1:1 mixture of ethyl acetate and 1M hydrochloric acid and stirred for 10 minutes. The phases are separated and the organic phase is back-extracted with 1M hydrochloric acid. The combined aqueous phases are adjusted to pH 6-7 with solid sodium bicarbonate and then extracted with dichloromethane-methanol 95:5. The combined organic phases are dried with sodium sulphate and evaporated. The title compound is obtained as a white foam from the residue by flash chromatography (SiO$_2$ 60F). Rf=0.51 (dichloromethane-methanol 9:1); Rt=2.08 (gradient I).

The following compounds are prepared in analogy to the process described in Example 1 (alternative synthesis):

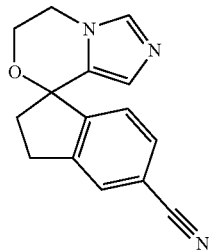

3 spiro-[(5,6-Dihydro-8H-imidazo[5,1-c][1,4]oxazine)-8,1'-(indane-5'-carbonitrile)]

starting from 1-oxo-indane-5-carbonitrile [25724-79-2]. Rf=0.39 (dichloromethane-methanol-25% aqueous ammonia solution 200:20:1); Rt=2.68 (gradient I)

Alternative Synthesis for Example 3:

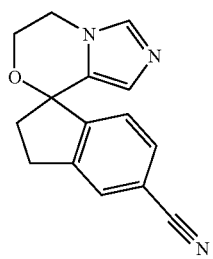

spiro-[(5,6-Dihydro-8H-imidazo[5,1-c][1,4]oxazine)-8,1'-(indane-5'-carbonitrile)]

0.04 mmol of tetrakis(triphenylphosphine)palladium is added to a mixture of 1.02 mmol of spiro-[(5,6-dihydro-8H-imidazo[5,1-c][1,4]oxazine)-8,1'-(5'-bromoindane)] and 0.68 mmol of zinc cyanide in 10 ml of absolute N,N-dimethylformamide. The reaction mixture is stirred at 80° C. for 1 hour and then evaporated. The title compound is obtained as a white foam from the residue by flash chromatography (SiO$_2$ 60F). Rf=0.39 (dichloromethane-methanol-25% aqueous ammonia solution 200:20:1); Rt=2.68 (gradient I).

The starting materials are prepared as follows:

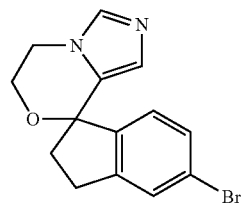

a) spiro[(5,6-Dihydro-8H-imidazo[5,1-c][1,4]oxazine)-8,1'-5'-bromoindane)]

The title compound is prepared from 5-bromoindan-1-one [34598-49-7] in analogy to the process described in Example 1 (alternative synthesis 1) and obtained as a yellowish oil. Rf=0.38 (dichloromethane-methanol-25% aqueous ammonia solution 200:20:1); Rt=3.31 (gradient I).

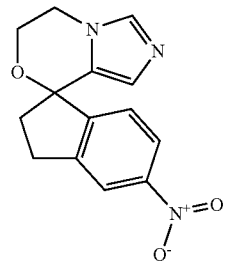

5 spiro[(5,6-Dihydro-8H-imidazo[5,1-c][1,4]oxazine)-8,1'-(5'-nitroindane)]

starting from 5-nitroindan-1-one [22246-24-8]

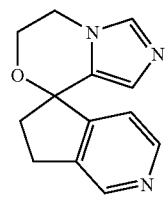

7 spiro-[(5,6-Dihydro-8H-imidazo[5,1-c][1,4]ox-azine)-8,5'-(6',7'-dihydro-5H-[2]pyrindine)]

starting from 6,7-dihydro-[2]pyrindin-5-one [350847-80-2]

Example 2

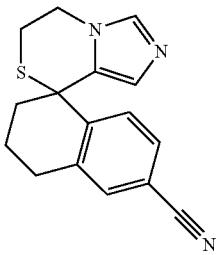

spiro-[(5,6-Dihydro-8H-imidazo[5,1-c][1,4]thiazine)-8,5'-(5',6',7',8'-tetrahydronaphthalene-2'-carbonitrile)]

A solution of 0.2 mmol of 2-[6-cyano-1-(1-trityl-1H-imidazol-4-yl)-1,2,3,4-tetrahydronaphthalen-1-ylsulphanyl] ethyl methane sulphonate in 5 ml of N,N-dimethylformamide is mixed with 1 mmol of caesium carbonate and heated at 80° C. for 3 hours. The reaction mixture is cooled to room temperature, diluted with water and extracted with ethyl acetate (2×). The combined organic phases are dried with sodium sulphate and evaporated. The title compound is identified from the residue on the basis of the Rf by flash chromatography (SiO$_2$ 60F).

The starting materials are prepared as follows:

a) 2-[6-Cyano-1-(1-trityl-1H-imidazol-4-yl)-1,2,3,4-tetrahydro-naphthalen-1-ylsulphanyl]-ethyl Methanesulphonate 5 mmol of triethylamine and 2 mmol of methanesulphonyl chloride are added to a solution of 1 mmol of 5-(2-hydroxyethylsulphanyl)-5-(1-trityl-1H-imidazol-4-yl)-5,6,7,8-tetrahydro-naphthalene-2-carbonitrile in 10 ml of dichloromethane at 0° C. The reaction mixture is stirred at 0° C. for 1 hour, diluted with dichloromethane, washed with 1N HCl, dried with sodium sulphate and evaporated. The crude title compound is identified on the basis of the Rf and used without further purification in the next stage.

b1) 5-(2-Hydroxyethylsulphanyl)-5-(1-trityl-1H-imidazol-4-yl)-5,6,7,8-tetrahydronaphthalene-2-carbonitrile 1.2 mmol of triphenylmethyl chloride [76-83-5] are added to a solution of 1.0 mmol of 5-(2-hydroxyethylsulphanyl-5-(1H-imidazol-4-yl)-5,6,7,8-tetrahydronaphthalene-2-carbonitrile and 1.5 mmol of triethylamine in 5 ml of dichloromethane at 0-5° C. The reaction solution is stirred at room temperature for 16 hours, poured into saturated aqueous sodium bicarbonate solution and extracted with dichloromethane. The combined organic phases are dried with sodium sulphate and evaporated. The title compound is identified from the residue on the basis of the Rf by flash chromatography (SiO$_2$ 60F).

c1) 5-(2-Hydroxyethylsulphanyl-5-(1H-imidazol-4-yl)-5,6,7,8-tetrahydronaphthalene-2-carbonitrile 5 mol % p-toluenesulphonic acid are added to a solution of 1 mmol of 5-hydroxy-5-(3H-imidazol-4-yl)-5,6,7,8-tetrahydronaphthalene-2-carbonitrile and 2.2 mmol of 2-mercaptoethanol [60-24-2] in 10 ml of xylene, and the mixture is heated to reflux in the presence of molecular sieves (4 Å) overnight. The reaction mixture is cooled to room temperature, diluted with 1M sodium bicarbonate solution and extracted with ethyl acetate (3×). The combined organic phases are dried with sodium sulphate and evaporated. The title compound is identified from the residue on the basis of the Rf by flash chromatography (SiO$_2$ 60F).

d1) 5-Hydroxy-5-(3H-imidazol-4-yl)-5,6,7,8-tetrahydronaphthalene-2-carbonitrile 3 ml of 2M HCl are added to a solution of 1 mmol of 5-hydroxy-5-(1-trityl-1H-imidazol-4-yl)-5,6,7,8-tetrahydronaphthalene-2-carbonitrile (Example 1d1) in 15 ml of tetrahydrofuran, and the mixture is heated to reflux for 2 hours. The reaction mixture is cooled to room temperature and evaporated. The residue is mixed with 1M sodium bicarbonate solution and extracted with dichloromethane. The combined organic phases are dried with sodium sulphate and evaporated. The title compound is identified from the residue on the basis of the Rf by flash chromatography (SiO$_2$ 60F).

Alternative Synthesis for 5-(2-hydroxyethylsulphanyl)-5-(1-trityl-1H-imidazol-4-yl)-5,6,7,8-tetrahydronaphthalene-2-carbonitrile b2) 5-(2-Hydroxyethylsulphanyl)-5-(1-trityl-1H-imidazol-4-yl)-5,6,7,8-tetrahydronaphthalene-2-carbonitrile The title compound is obtained in analogy to Example 1b1 starting from ethyl [6-cyano-1-(1-trityl-1H-imidazol-4-yl-1,2,3,4-tetrahydronaphthalen-1-ylsulphanyl]acetate.

c2) Ethyl [6-cyano-1-(1-trityl-1H-imidazol-4-yl)-1,2,3,4-tetrahydronaphthalen-1-ylsulphanyl]-acetate The title compound is obtained in analogy to Example 1c1 starting from 5-mercapto-(1-trityl-1H-imidazol-4-yl)-5,6,7,8-tetrahydronaphthalene-2-carbonitrile.

e2) 5-Mercapto-5-(1-trityl-1H-imidazol-4-yl)-5,6,7,8-tetrahydronaphthalene-2-carbonitrile A solution of 1 mmol of 5-hydroxy-5-(1-trityl-1H-imidazol-4-yl)-5,6,7,8-tetrahydronaphthalene-2-carbonitrile (Example 1d1) and 0.5 mmol of 2,4-bis(4-methoxyphenyl)-1,3,2,4-dithiadiphosphetane 2,4-disulphide (Lawesson's reagent) [19172-47-5] in 10 ml of toluene is heated to reflux for 2 hours. The reaction mixture is cooled to room temperature and evaporated. The title compound is identified from the residue on the basis of the Rf by flash chromatography (SiO$_2$ 60F).

Alternative Synthesis for Ethyl [6-cyano-1-(1-trityl-1H-imidazol-4-yl)-1,2,3,4-tetrahydro-naphthalen-1-ylsulphanyl]acetate c3) Ethyl [6-cyano-1-(1-trityl-1H-imidazol-4-yl)-1,2,3,4-tetrahydronaphthalen-1-ylsulphanyl]-acetate The title compound is obtained in analogy to Example 2b1 starting from ethyl [6-cyano-1-(1H-imidazol-4-yl)-1,2,3,4-tetrahydronaphthalen-1-ylsulphanyl]acetate.

d3) Ethyl [6-cyano-1-(1H-imidazol-4-yl)-1,2,3,4-tetrahydronaphthalen-1-ylsulphanyl]-acetate A solution of 1.00 mmol of 5-hydroxy-5-(3H-imidazol-4-yl)-5,6,7,8-tetrahydronaphthalene-2-carbonitrile (Example 2c1) and 10 mmol of ethyl mercaptoacetate [623-51-8] in 2 ml of trifluoroacetic acid is stirred at 70° C. for 24 hours. The reaction mixture is cooled to room temperature, poured into ice-water and neutralized with 4M sodium hydroxide solution. The mixture is extracted with ethyl acetate, and the combined organic phases are dried with sodium sulphate and evaporated. The title compound is identified from the residue on the basis of the Rf by flash chromatography (SiO$_2$ 60F).

The following compounds are prepared in analogy to the process described in Example 2:

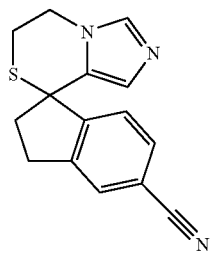

4 spiro[(5,6-Dihydro-8H-imidazo[5,1-c][1,4]thiazine)-8,1'-(indane)-5'-carbonitrile)]

starting from 1-oxo-indane-5-carbonitrile [25724-79-2]

6 spiro-[(5,6-Dihydro-8H-imidazo[5,1-c][1,4]thiazine)-8,1'-(5'-fluoroindane)]

starting from 5-fluoroindan-1-one [700-84-5]

Example 8

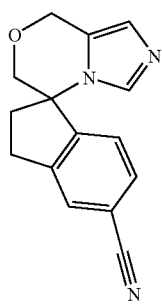

spiro[(5,6-Dihydro-8H-imidazo[5,1-c][1,4]oxazine)-5,1'-(5'-cyanoindane)]

A solution of 1 mmol of spiro-[(5,6-dihydro-8H-imidazo[5,1-c][1,4]oxazine)-5,1'-(5'-trifluoro-methanesulphonyloxyindane)] in 20 ml of toluene is mixed with 2 mmol of zinc cyanide and 5 mol % of tetrakis(triphenylphosphine)palladium, degassed and heated at 120° C. for 20 hours. The reaction solution is cooled and stirred with water and tert-butyl methyl ether. The phases are separated and the aqueous phase is extracted with tert-butyl methyl ether (2×). The organic phases are combined and evaporated to dryness. The title compound is identified from the residue on the basis of the Rf by flash chromatography (SiO$_2$ 60F).

The starting materials are prepared as follows:

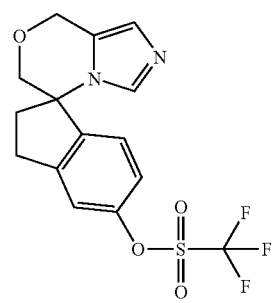

a) spiro-[(5,6-Dihydro-8H-imidazo[5,1-c][1,4]oxazine)-5,1'-(5'-trifluoromethanesulphonyloxy-indane)]

2.2 mmol of N-phenylbis(trifluoromethanesulphonyl)amine) and 2.5 mmol of triethylamine are added to a solution of 2 mmol of spiro-[(5,6-dihydro-8H-imidazo[5,1-c][1,4]oxazine)-5,1'-(5'-hydroxyindane)] in 20 ml of dichloromethane under argon. The reaction solution is stirred at room temperature for 18 hours and then evaporated to dryness. The title compound is identified from the residue on the basis of the Rf by flash chromatography (SiO$_2$ 60F).

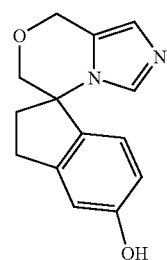

b) spiro-[(5,6-Dihydro-8H-imidazo[5,1-c][1,4]oxazine)-5,1'-(5'-hydroxyindane)]

A mixture of 3.6 mmol of spiro-[(5,6-dihydro-8H-imidazo[5,1-c][1,4]oxazine)-5,1'-(5'-methoxyindane)] and 10 ml of trimethylsilyl iodide in 40 ml of acetonitrile is heated to reflux for 24 hours. 10 ml of methanol are cautiously added, and the mixture is heated to reflux for a further 30 minutes. The reaction mixture is evaporated. The title compound is identified from the residue on the basis of the Rf by flash chromatography (SiO$_2$ 60F).

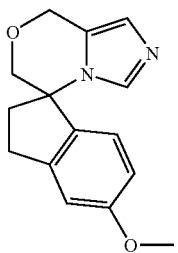

c) spiro-[(5,6-Dihydro-8H-imidazo[5,1-c][1,4]oxazine)-5,1'-(5'-methoxyindane)]

A mixture of 1.9 mmol of spiro-[(5,6,8,8a-tetrahydro-1H-imidazo[5,1-c][1,4]oxazine)-5,1'-(5'-methoxyindane)] and 1 g of manganese dioxide in 50 ml of toluene is heated to reflux for 0.5 hour. The reaction mixture is cooled to room temperature, the solid is filtered off through Hyflo, and the filtrate is evaporated. The title compound is identified from the residue on the basis of the Rf by flash chromatography (SiO$_2$ 60F).

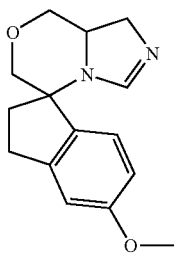

d) spiro-[(5,6,8,8a-Tetrahydro-1H-imidazo[5,1-c][1,4]oxazine)-5,1'-(5'-methoxyindane)]

A solution of 31 mmol of spiro-[(3-aminomethyl)morpholine)-5,1'-(5'-methoxyindane)] and 31 mmol of N,N-dimethylformamide dimethyl acetal in 50 ml of dichloromethane is heated to reflux for 6 hours. The reaction mixture is cooled to room temperature and evaporated. The crude title compound is identified from the residue on the basis of the Rf. The title compound is employed without further purification in the next stage.

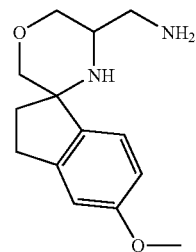

e1) spiro-[(3-(Aminomethyl)morpholine)-5,1'-(5'-methoxyindane)]

A mixture of 50 mmol of spiro-[(3-[1-nitromethylidene]morpholine)-5,1'-(5'-methoxyindane)] and 5 teaspoonsful of Raney nickel in 500 ml of tetrahydrofuran and 250 ml of methanol is hydrogenated under atmospheric pressure for 5 hours. The reaction mixture is filtered through Hyflo and the filtrate is evaporated. The crude title compound is identified from the residue on the basis of the Rf. The title compound is employed without further purification in the next stage.

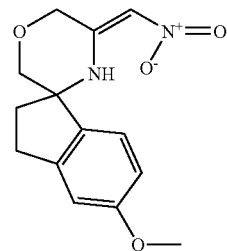

f1) spiro-[(3-[1-Nitromethylidene]morpholine)-5,1'-(5'-methoxyindane)]

A mixture of 100 mmol of spiro-[(3-(N-nitroso-N-methylamino)-5,6-dihydro-2H-[1,4]oxazine)-5,1'-(5'-methoxyindane)], 200 ml of N,N-dimethylformamide, 50 ml of nitromethane and 115 mmol of potassium tert-butoxide is stirred at room temperature for 15 minutes. The mixture is quenched by adding 20 ml of glacial acetic acid and is diluted with dichloro methane and water. The organic phase is separated off, washed with water, dried with sodium sulphate and evaporated. The title compound is identified from the residue on the basis of the Rf by flash chromatography (SiO2 60F).

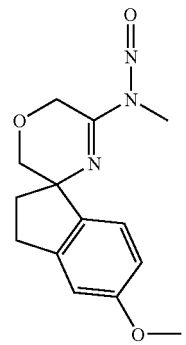

g) spiro-[(3-(N-Nitroso-N-methylamino)-5,6-dihydro-2H-[1,4]oxazine)-5,1'-(5'-methoxy-indane)]

125 mmol of sodium nitrite are added in portions to a solution of 100 mmol of spiro-[(3-(N-methylamino)-5,6-dihydro-2H-[1,4]oxazine)-5,1'-(5'-methoxyindane)] in 200 ml of glacial acetic acid at room temperature. The reaction mixture is stirred for 1.5 hours. It is diluted with dichloromethane and water. The organic phase is separated off, washed with water, dried with sodium sulphate and evaporated. The title compound is identified from the residue on the basis of the Rf by flash chromatography (SiO$_2$ 60F).

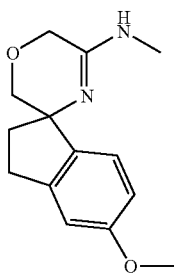

h) spiro-[(3-(N-Methylamino)-5,6-dihydro-2H-[1,4]oxazine)-5,1'-(5'-methoxyindane)]

A solution of 69.5 mmol of spiro-[(morpholin-3-one)-5,1'-(5'-methoxyindane)] in 200 ml of tetrahydrofuran and 25 ml of benzene is cooled to 0° C. and saturated with methylamine. A solution of 19 g of titanium tetrachloride in 25 ml of benzene is added dropwise over the course of 15 minutes. After the addition is complete, the reaction mixture is heated to reflux for 3 hours. The reaction mixture is then cooled to 0° C. and cautiously quenched with 60 ml of water. It is filtered through Hyflo, and the filter cake is washed several times with tetrahydrofuran. The phases of the filtrate are separated, and the organic phase is dried with sodium sulphate and evaporated. The title compound is identified from the residue on the basis of the Rf by flash chromatography (SiO$_2$ 60F).

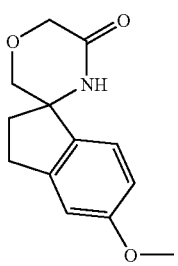

i) spiro-[(Morpholin-3-one)-5,1'-(5'-methoxyindane)]

A solution of 97.3 mmol of potassium tert-butoxide in 180 ml of tert-amyl alcohol is mixed at room temperature with 39.0 mmol of 2-chloro-N-(1-hydroxymethyl-5-methoxyindan-1-yl)-acetamide and stirred for 2 hours. The reaction mixture is poured into water and extracted with tert-butyl methyl ether. The combined organic phases are washed with brine, dried with sodium sulphate and evaporated. The title compound is obtained as a beige solid which is employed without further purification for the next stage. Rf=0.21 (ethyl acetate-heptane 2:1); Rt=2.98 (gradient I).

j) 2-Chloro-N-(1-hydroxymethyl-5-methoxyindan-1-yl)acetamide

A solution of 60.0 mmol of (1-amino-5-methoxyindan-1-yl)methanol in 120 ml of acetonitrile and 40 ml of methanol is cooled to −10° C. and 69 mmol of triethylamine and, dropwise over the course of 1 hour, 80.5 mmol of chloroacetyl chloride are successively added. The reaction mixture is warmed to room temperature and stirred for 3 hours. The reaction mixture is poured into water and extracted with tert-butyl methyl ether. The combined organic phases are washed with brine, dried with sodium sulphate and evaporated. The title compound is obtained as a beige solid which is employed without further purification for the next stage. Rf=0.15 (ethyl acetate-heptane 1:1); Rt=3.01 (gradient I).

k) (1-Amino-5-methoxyindan-1-yl)methanol

A suspension of 168 mmol of lithium aluminium hydride in 300 ml of tetrahydrofuran is cooled to 0-5° C. 80.0 mmol of 1-amino-5-methoxyindane-1-carboxylic acid are added in portions, and the reaction mixture is then heated to reflux for 1 hour. The reaction mixture is cooled to room temperature and quenched with 7.8 ml of water, 36.2 ml of 1M sodium hydroxide solution and a further 21.0 ml of water. The reaction mixture is stirred at room temperature for 30 minutes and then filtered through Hyflo. The filtrate is evaporated. The title compound is obtained as a beige solid which is employed without further purification for the next stage. Rt=2.36 (gradient III).

l) 1-Amino-5-methoxyindane-1-carboxylic Acid 748 mmol of barium hydroxide octahydrate are added to a suspension of 187 mmol of 2',3'-dihydro-5'-methoxyspiro[imidazolidine-4,1'-[1H]indane]-2,5-dione [66892-41-9] in 1200 ml of water. The reaction mixture is heated to reflux for 4 days, cooled and adjusted to pH=2 by dropwise addition of concentrated sulphuric acid. The suspension is filtered through Hyflo and the filter cake is washed with water. The filtrate is adjusted to pH 9.5 with concentrated aqueous ammonium hydroxide solution and concentrated to a remaining volume of about 300 ml. The residue is stirred at room temperature for 16 hours, the precipitated solid is filtered off, Alternative Syntheses for spiro-[(3-(aminomethyl) morpholine)-5,1'-(5'-methoxyindane)]

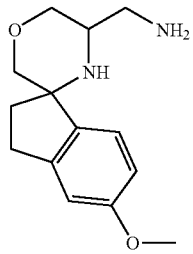

e2) spiro-[(3-(Aminomethyl)morpholine)-5,1'-(5'-methoxyindane)]

A mixture of 40.1 mmol of spiro-[(3-(cyano)morpholine)-5,1'-(5'-methoxyindane)] and 2 g of Raney nickel (activated by washing with water to pH 7 and subsequent washing with ethanol) in 200 ml ethanol is hydrogenated under a pressure of 500 psi for 12 hours. The reaction mixture is filtered through Hyflo and the filtrate is evaporated. The crude title compound is identified from the residue on the basis of the Rf. The title compound is employed without further purification in the next stage.

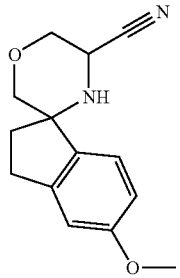

f2) spiro-[(3-(Cyano)morpholine)-5,1'-(5'-methoxyindane)]

7.8 ml of ethyl acetate are added to a solution of 160 mmol of lithium aluminium hydride (1M in hexane) in 750 ml of tetrahydrofuran at 0° C., and the mixture is stirred at 0° C. for 2 hours. A solution of 20 mmol of spiro[(morpholin-3-one)-5,1'-(5'-methoxyindane)] (Example 81) in 250 ml of tetrahydrofuran is added dropwise to this solution, and the reaction mixture is stirred at 0° C. for 45 minutes. 600 ml of glacial acetic acid and then 120 mmol of a 4.5M aqueous potassium cyanide solution are added. The mixture is stirred at room temperature for 16 hours. The reaction mixture is diluted with 1M sodium bicarbonate solution and extracted with ethyl acetate-tetrahydrofuran 1:1 (3×). The combined organic phases are washed with brine, dried with sodium sulphate and evaporated. The title compound is identified from the residue on the basis of the Rf by flash chromatography (SiO₂ 60F).

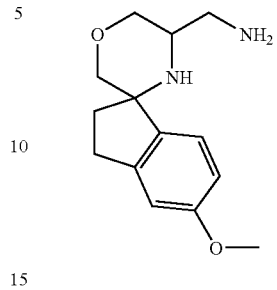

e3) spiro-[(3-(Aminomethyl)morpholine)-5,1'-(5'-methoxyindane)]

3.00 mmol of lithium aluminium hydride are added in portions to a solution of 1.00 mmol of spiro-[(3-(cyano)morpholine)-5,1'-(5'-methoxyindane)] (Example 8 f2) in 5 ml of tetrahydro furan at 0° C. The reaction mixture is stirred at room temperature for 30 minutes and then quenched with 0.25 ml of methanol. The mixture is mixed with 20 ml of dichloromethane, 20 mg of solid potassium carbonate and 0.30 ml of water and filtered through Hyflo. The filter cake is washed with dichloromethane and the filtrate is evaporated. The title compound is identified from the residue on the basis of the Rf by flash chromatography (SiO₂ 60F).

Alternative Syntheses for spiro-[(3-cyano)morpholine)-5,1'-5'-methoxyindane)]

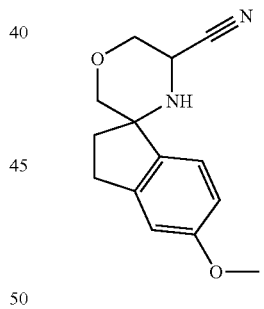

f3) spiro-[(3-(Cyano)morpholine)-5,1'-(5'-methoxyindane)]

1.8 ml of trifluoroacetic acid are added to a solution of 0.51 mmol of spiro-[(3-(cyano) morpholine)-5,1'-(5'-methoxyindane)-4-carboxylic acid tert-butyl ester] in 1.8 ml of dichloromethane at 0° C. The reaction mixture is stirred at 0° C. for 2 hours and then poured into saturated aqueous sodium bicarbonate solution and extracted with tert-butyl methyl ether. The combined organic phases are dried with sodium sulphate and evaporated. The title compound is obtained as a brown resin from the residue by flash chromatography (SiO₂ 60F). Rf=0.52 (dichloromethane-methanol-25% aqueous ammonia solution 200:2:1); Rt=2.78 (gradient I).

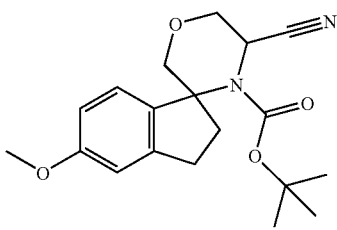

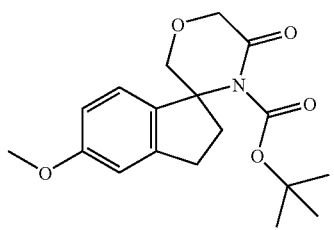

g3) spiro-[(3-Cyano)morpholine)-5,1'-(5'-methoxy-indane)-4-carboxylic Acid tert-butyl Ester]

A solution of 1.22 mmol of spiro-[(3-(hydroxy)morpholine)-5,1'-(5'-methoxyindane-4-carboxylic acid tert-butyl ester] in 5 ml of absolute acetonitrile is cooled to −30° C.-40° C. 6.11 mmol of trimethylsilyl cyanide and 0.10 mmol of scandium triflate are added to the reaction solution, and the mixture is stirred at −30° C.--40° C. for 1 hour. The reaction solution is mixed with saturated aqueous sodium bicarbonate solution and extracted with dichloromethane. The combined organic phases are washed with brine, dried with sodium sulphate and evaporated. The title compound is obtained as a yellowish resin from the residue by flash chromatography (SiO$_2$ 60F). Rf=0.41 (ethyl acetate-heptane 1:1); Rt=4.68 (gradient I).

i3) spiro-[(Morpholin-3-one)-5,1'-(5'-methoxyindane)-4-carboxylic Acid tert-butyl Ester]

2.34 mmol of n-butyllithium solution (1.7M in hexane) are added dropwise to a solution of 2.14 mmol of spiro-[(morpholin-3-one)-5,1'-(5'-methoxyindane)] (Example 8i) in 14 ml of absolute tetrahydrofuran at −78° C. under argon. The reaction solution is stirred at −78° C. for 30 minutes and then a solution of 2.88 mmol of di-tert-butyl dicarbonate is added. The reaction solution is thawed to room temperature and stirred at this temperature for 1 hour. The reaction mixture is poured into saturated aqueous ammonium chloride solution and extracted with tert-butyl methyl ether. The combined organic phases are washed with brine, dried with sodium sulphate and evaporated. The title compound is obtained as a yellowish resin from the residue by flash chromatography (SiO$_2$ 60F). Rf=0.16 (ethyl acetate-heptane 1:2); Rt=4.25 (gradient I).

The following compound is prepared in analogy to the processes described in Example 8:

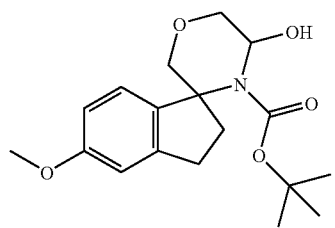

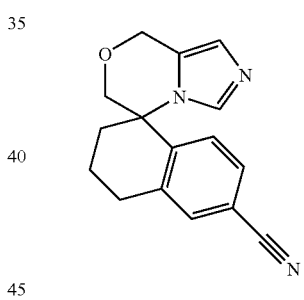

h3) spiro-[(3-(Hydroxy)morpholine)-5,1'-(5'-methoxyindane)-carboxylic Acid tert-butyl Ester]

3.55 mmol of diisobutyl aluminium hydride solution (1M in dichloromethane) are added dropwise to a solution of 1.41 mmol of spiro-[(morpholin-3-one)-5,1'-(5'-methoxyindane)-4-carboxylic acid tert-butyl ester] in 5 ml of absolute tetrahydrofuran at −78° under argon. The reaction solution is stirred at −78° C. for 1 hour and then quenched with 0.30 ml of methanol. The mixture is poured into aqueous 1M Rochelle salt solution and extracted with tert-butyl methyl ether. The combined organic phases are washed with brine, dried with sodium sulphate and evaporated. The title compound is obtained as brown resin and employed without further purification for the next stage. Rt=4.04 (gradient I).

9 spiro-[(5,6-Dihydro-8H-imidazo[5,1-c][1,4]oxazine)-5,1'-(6'-cyano-1',2',3',4'-tetrahydronaphthalene)]

starting from (1-amino-6-methoxy-1,2,3,4-tetrahydronaphthalen-1-yl)methanol [153707-95-0]

Example 10

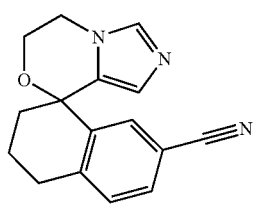

spiro-[(5,6-Dihydro-8H-imidazo[5,1-c][1,4]oxazine)-8,8'-(5',6',7',8'-tetrahydronaphthalene-2'-carbonitrile)]

The title compound is prepared in analogy to Example 1 (alternative synthesis) starting from 8-oxo-5,6,7,8-tetrahydronaphthalene-2-carbonitrile [776328-39-3]. Rf=0.24 (dichloromethane-methanol-25% aqueous ammonia solution 200:10:1); Rt=2.89 (gradient I).

Alternative Synthesis for Example 10:

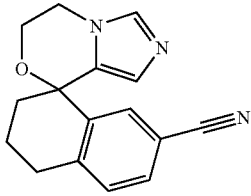

spiro-[(5,6-Dihydro-8H-imidazo[5,1-c][1,4]oxazine)-8,8'-(5',6',7',8'-tetrahydronaphthalene-2'-carbonitrile)]

A solution of 1.27 mmol of spiro-[(5,6-dihydro-8H-imidazo[5,1-c][1,4]oxazine)-8,8'-(7'-iodo-5',6',7',8'-tetrahydronaphthalene-2'-carbonitrile)] and 1.80 mmol of tributyltin hydride in 10 ml of absolute dichloromethane is heated to reflux for 2 hours. The reaction solution is cooled and mixed with 10 ml of 1M sodium hydroxide solution. The reaction mixture is vigorously stirred at room temperature for 1 hour, and the phases are then separated. The organic phase is washed with brine, dried with sodium sulphate and evaporated. The title compound is obtained as a white solid from the residue by flash chromatography (SiO$_2$ 60F) and subsequent stirring with diethyl ether. Rf=0.24 (dichloromethane-methanol-25% aqueous ammonia solution 200:10:1); Rt=2.89 (gradient I).

The starting materials are prepared as follows:

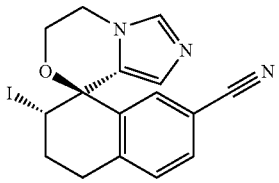

a2) spiro-[(5,6-Dihydro-8H-imidazo[5,1-c][1,4]oxazine)-8,8'-(7'-iodo-5',6',7',8'-tetrahydronaphthalene-2'-carbonitrile)]

The title compound is prepared in analogy to Example 1a2 starting from 8-oxo-5,6,7,8-tetrahydronaphthalene-2-carbonitrile [776328-39-3].

Example 11

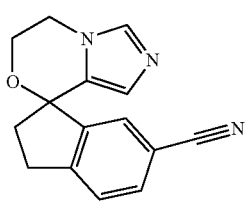

spiro-[(5,6-Dihydro-8H-imidazo[5,1-c][1,4]oxazine)-8,1'-(indane-6'-carbonitrile)]

The title compound is prepared in analogy to Example 3 (alternative synthesis) starting from 6-bromoindan-1-one [14548-39-1].

The invention claimed is:
1. A compound of the formula

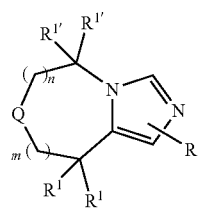

(I)

in which
R is deuterium, halogen or hydrogen;
a) $R^1$ is in each case hydrogen, and $R^{1'}$ and $R^{1'}$ are together a radical of the formula

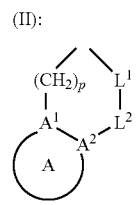

(II):

or
b) $R^1$ and $R^1$ are together a radical of the formula

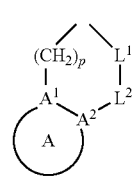

(II)

and $R^{1'}$ is in each case hydrogen,
and for both a) and b):
$A^1$ and $A^2$ are two ortho ring atoms, and A is aryl or heterocyclyl, which radicals are unsubstituted or substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$-alkylsilyl, trifluoromethoxy or trifluoromethyl;
$L^1$ is —CH$_2$—, —CH$_2$—CH$_2$—, —CH=CH—, —CH=N—, —CH$_2$—CH=N—, —CH=N—O—, —CH$_2$—CH=N—O—, —CH$_2$—O—, —CH$_2$—CH$_2$—O—, —CH=CH—O—, —CH$_2$—S—, —CH$_2$—CH$_2$—S—, —CH=CH—S—, —CH$_2$—NH—, —CH$_2$—CH$_2$—NH—, —CH=CH—NH—, —CH$_2$—NH—O—, —CH$_2$—CH$_2$—NH—O—, —CH=CH—NH—O—, —CH$_2$—O—NH—, —CH$_2$—CH$_2$—O—NH—, —CH=CH—O—NH—, —CH$_2$—N=N—, —CH$_2$—CH$_2$—N=N—, —CH=CH—N=N—, —CH$_2$—S(O)—, —CH$_2$—CH$_2$—S(O)—, —CH=CH—S(O)—, —CH$_2$—SO$_2$—, —CH$_2$—CH$_2$—SO$_2$—, —CH=CH—SO$_2$—, —O—, —S—, —NH—, —NH—O—, —O—NH—, —N=N—, —S(O)— or —SO$_2$—, which radicals are unsubstituted or substituted by 1-3 R$^3$;

L$^2$ is —CH$_2$—, —CH$_2$—CH$_2$—, —CH=CH— or, if L$^1$ is —CH$_2$—, —CH$_2$—CH$_2$— or —CH=CH—, is also —N=CH—, —N=CH—CH$_2$—, —O—N=CH—CH$_2$ or —O—N=CH—, which radicals are unsubstituted or substituted by 1-3 R$^3$ or, if L$^1$ is not —O—, —S—, —NH—, —NH—O—, —O—NH—, —N=N—, —S(O)— or —SO$_2$—, is also a bond;

R$^3$ is C$_1$-C$_8$ alkoxy, C$_1$-C$_8$ alkoxycarbonyl, C$_1$-C$_8$ alkyl, C$_0$-C$_8$ alkylcarbonyl or C$_1$-C$_8$ alkylsulphonyl;

Q is oxygen or sulphur;

m is a number 0, 1 or 2;

n is a number 0, 1 or 2;

p is a number 0, 1, 2, 3 or 4;

where m and n are not simultaneously 0 and, if R$^1$ is hydrogen, n is 1 or 2;

or a pharmaceutically acceptable salt thereof.

2. A compound according to claim 1, which corresponds to the formula

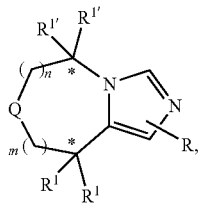

(Ia)

or a pharmaceutically acceptable salt thereof, where the meanings of the substituents R, R$^1$, R$^{1'}$, Q, m and n are as indicated for compounds of the formula (I) according to claim 1, and * designates an asymmetric carbon atom at the C atom for which the respective pairs of R$^1$ and R$^{1'}$ substituents are not both hydrogen.

3. A compound according to claim 1, where R is deuterium or hydrogen.

4. A compound according to claim 1, where A is optionally substituted 4-acetylphenyl, 4-cyanophenyl, 4-methanesulphonylphenyl, 4-methoxyphenyl, 4-nitrophenyl, 4-heterocyclylphenyl, where the heterocycle preferably comprises at least one nitrogen atom, or pyridyl.

5. A compound according to claim 1, where the group -L$^1$-L$^2$- is C$_1$-C$_4$ alkylene which is optionally substituted by 1-3 C$_1$-C$_8$ alkoxy, C$_1$-C$_8$ alkoxycarbonyl, C$_1$-C$_8$ alkyl, C$_0$-C$_8$ alkylcarbonyl or C$_1$-C$_8$ alkylsulphonyl.

6. A compound according to claim 1, where n is 1.

7. A compound according to claim 1, where p is 0.

8. A pharmaceutical composition comprising a compound of the general formula (I) or a pharmaceutically acceptable salt thereof according to claim 1, and conventional excipients.

9. A pharmaceutical composition comprising a compound of the general formula (Ia) or a pharmaceutically acceptable salt thereof according to claim 2, and conventional excipients.

10. A pharmaceutical composition in the form of a product or of a kit composed of individual components consisting a) of a compound of the general formula (I) or a pharmaceutically acceptable salt thereof according to claim 1, and b) at least one pharmaceutical form whose active ingredient has a blood pressure-lowering, an inotropic, a metabolic or a lipid-lowering effect.

11. A pharmaceutical composition in the form of a product or of a kit composed of individual components consisting a) of a compound of the general formula (Ia) or a pharmaceutically acceptable salt thereof according to claim 2, and b) at least one pharmaceutical form whose active ingredient has a blood pressure-lowering, an inotropic, a metabolic or a lipid-lowering effect.

* * * * *